United States Patent [19]
Jenkins

[11] Patent Number: 4,772,794
[45] Date of Patent: Sep. 20, 1988

[54] APPARATUS FOR THE DETECTION OF AIRBORNE LOW VOLATILITY VAPORS

[75] Inventor: Anthony Jenkins, Little Shelford, England

[73] Assignee: Analytical Instruments Ltd., Pampisford, England

[21] Appl. No.: 844,857

[22] Filed: Mar. 27, 1986

[30] Foreign Application Priority Data

May 30, 1985 [GB] United Kingdom ............... 8513687

[51] Int. Cl.$^4$ ........................................... G01N 30/70
[52] U.S. Cl. ................................. 250/382; 250/283; 250/288
[58] Field of Search ............... 250/382, 288 R, 288 A, 250/427, 326, 283; 55/390, 406

[56] References Cited
U.S. PATENT DOCUMENTS

| 4,242,107 | 12/1980 | Jenkins | 55/18 |
| 4,259,572 | 3/1981 | Brunnee et al. | 250/281 |
| 4,468,468 | 8/1984 | Benninghoven et al. | 436/173 |

Primary Examiner—Janice A. Howell
Assistant Examiner—Constantine Hannaher
Attorney, Agent, or Firm—Anthony J. Casella; Gerald E. Hespos

[57] ABSTRACT

An apparatus for the detection of airborne, low volatility materials, comprising a mobile carrier, preferably made of silica, onto which material to be detected is caused to be deposited. The mobile carrier is arranged to carry the material to the first location where unwanted volatile materials are purged from the trap, then to a second location where the remaining material is caused to be ionized and then to a third location where the ionized material is caused to be lifted off the carrier into an ion collector.

20 Claims, 3 Drawing Sheets

APPARATUS FOR THE DETECTION OF AIRBORNE LOW VOLATILITY VAPORS

The present invention is concerned with an apparatus for the detection of airborne low volatility vapours.

Our British Pat. No. 1 578 533 describes apparatus which samples the air, traps out low volatility compounds of interest in a rotating trap and subsequently desorbs the trapped components into a detector. The detector normally employed is an electron capture detector and this apparatus is used to monitor the atmosphere for the presence of low volatility electrophylic compounds at concentration levels approaching 1 part per trillion ($10^{-12}$) in the atmosphere.

There has arisen a need to detect such compounds at levels approaching 1 part in $10^{15}$ part of air and the apparatus described in U.K. Pat. No. 1 578 533 is capable of only limited further improvement in detection capability.

The present invention seeks to improve the detection capability by improving the trapping efficiency and reducing noise levels in the detector so that concentrations of 1 part of certain material may be detected in $10^{15}$ parts of air.

In accordance with one aspect of the present invention, there is provided an apparatus for the detection of airborne, low volatility materials, comprising a mobile carrier onto which material to be detected is caused to be deposited, the mobile carrier being arranged to carry said material to a first location where unwanted volatile materials are purged from the trap and then to a second position where the remaining material is caused to be ionized and then to a third location where the ionized material is caused to be lifted off the carrier into an ion collector.

The ion current is indicative of the concentration of low volatility electrophylic species in the sampled air.

Preferably, the mobile carrier is a rotating disc or moving belt made of an electrical insulating material, e.g. quartz, P.T.F.E., PERSPEX, glass, ceramics and the like.

Preferably, the ionized material on the carrier is lifted off the carrier into the ion collector in the form of an ion drift tube by means of pulsed radiation, e.g. from pulsed arc light or laser, whereby to produce "packets" of ions which are caused to drift down the drift tube under the influence of an electric field.

In accordance with a second aspect of the present invention, there is provided an ion drift detector for use in the detection of airborne, low volatility materials, wherein said airborne low volatility materials are arranged to be trapped on the surface of a solid mobile carrier of an electrically insulating material, said surface being displaceable to a position opposite one end of the drift tube such that the ions can be released from said surface by the heating effect of radiated pulses from a pulsed electromagnetic radiation source disposed adjacent the other end of the drift tube.

In a preferred embodiment, the ion drift detector comprises a cylindrical drift tube which is made of an electrically insulating material and which is closed at one end and open at the other, a pulsed radiation source and a collector electrode disposed within the drift tube, means for establishing a flow of drift gas through the tube towards the open end, and a solid mobile carrier of an electrically insulating material which is adapted to trap and hold ions of said low volatility materials in its surface, said surface being displaceable to a position adjacent to and facing the open end of the drift tube, and means establishing an electric field within the tube which causes ions released from said surface by the heating effect of pulsed light from said light source to drift up the tube, against the flow of drift gas, towards said collector electrode.

In accordance with a third aspect of the present invention, there is provided an apparatus for the detection of airborne, low volatility materials, comprising a mobile carrier surface onto which molecules of a material or materials to be detected are caused to be deposited, means for ionizing said molecules in the carrier surface by causing said surface to be sprayed with electrons from a corona discharge device, means for subsequently stripping excess electrons from the surface, and a drift tube detector for detecting ions present on said surface.

The invention is described further hereinafter, by way of example only, with reference to the accompanying drawings, in which.

Figure 1:
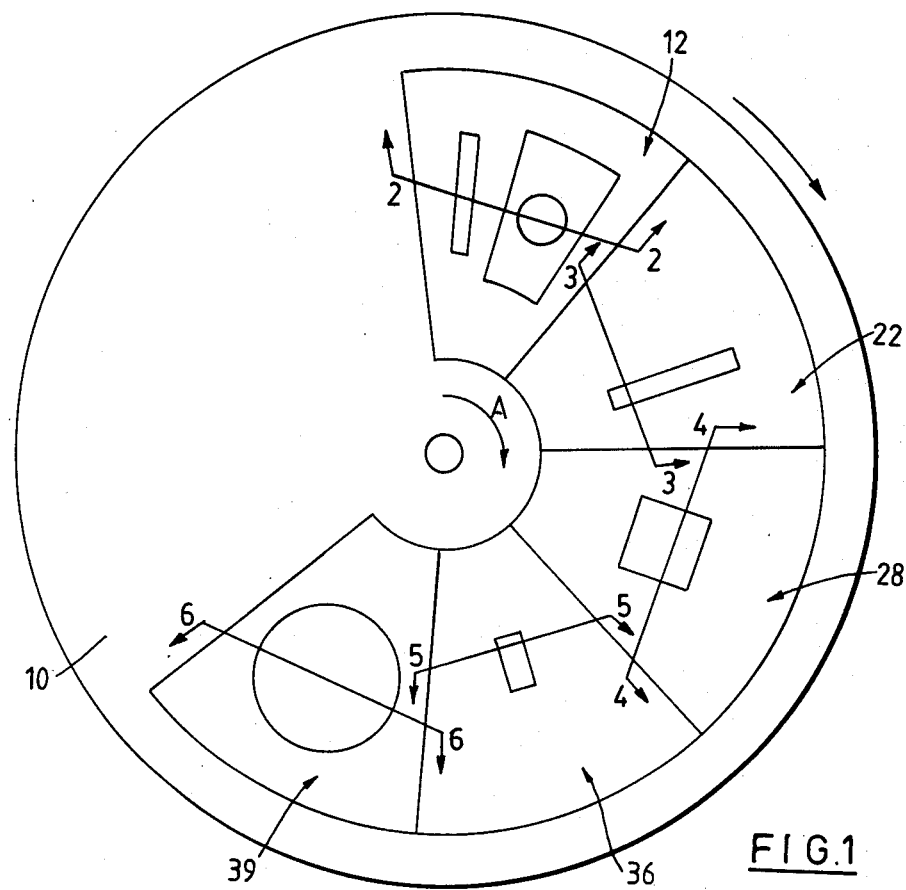
FIG. 1 is a highly diagrammatic front view of an apparatus embodying the present invention.

Referring first to FIGS. 1 to 6, the illustrated embodiment of the apparatus includes a mobile trap 10 which may be in the form of a linearly moving belt or, as shown in FIG. 1, a rotating disc. The trap is made from an electrically insulating material and is preferably in the form of a thin flat disc of silica which is rotatable about its central axis in the direction of arrow A (FIG. 1).

Figure 2:
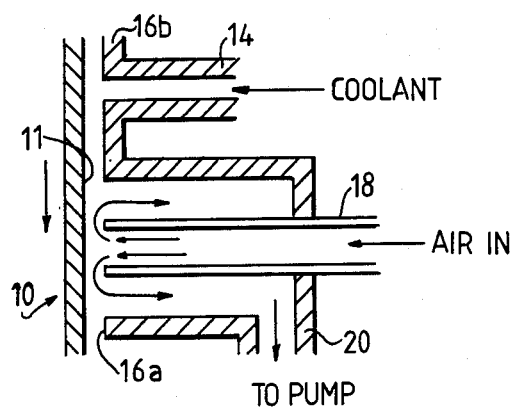
FIGS. 2 to 6 are diagrammatic sectional views illustrating various component parts of an apparatus embodying the present invention and taken on lines 2—2, 3—3, 4—4, 5—5, 6—6, respectively, in FIG. 1.

The section of FIG. 2 shows in diagrammatic form an ion trapping region 12 of the apparatus. Coolant gas (e.g. liquid nitrogen or carbon dioxide), is piped into the trap region 12 via an inlet 14 to cool the region 12 to, or below, room temperature and to provide a curtain effect to prevent ingress of external air around edge flanges 16a, 16b. By virtue of the rotation of the disc 10, the trap 10 is rotated through the coolant and into the trapping region 12 where air to be sampled is blown at the surface 11 of the disc 10 (right-hand surface, as viewed in FIG. 2) via a second inlet pipe 18, and exhausts through an outlet pipe 20 to a large volume pump, capable of sampling, say, 2 cu.ft per second against a back pressure of, for example, up to 20" of water. Any low volatility contaminants entering on the air stream will strike the cold silica surface 11 and be trapped therein. The heat of absorption of a low volatility nitro molecule, such as $CH_3C_6H_2(NO_2)_3$, in the surface 11 has been shown to be about 22 Kcal/mole. This ensures that, once trapped, such a molecule will not easily be eluted in the very high air stream as it passes through the trap. Using this technique, at very low concentration, high trapping efficiencies can be obtained, depending on trap temperature, air flow and the probability of striking the trap surface 11.

Figure 3:
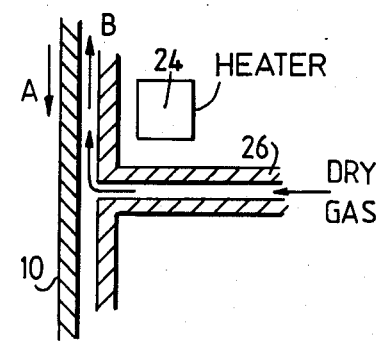

In the event that it is found to be necessary to remove most of the more volatile impurities from the trap surface, this can be achieved in a pre-stripper region 22 as illustrated in FIG. 3. As the silica trap rotates through the pre-stripper region 22, a heater 24 increases the temperature of the trap surface and a flow of dry purge gas such a nitrogen or dry air introduced via a pipe 26, is maintained in a direction B counter to the direction A. Many volatile contaminants will be removed in this pre-stripper stage, leaving only low volatility components remaining on the trap surface.

Figure 4:
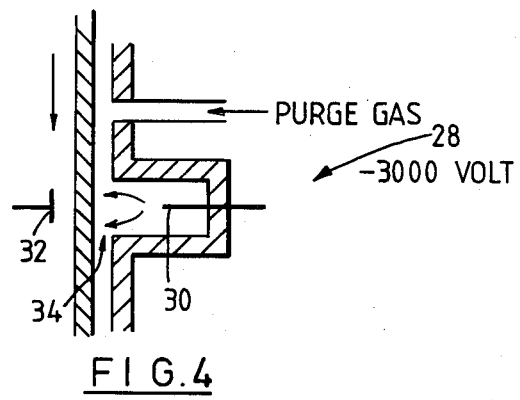
Figure 5:
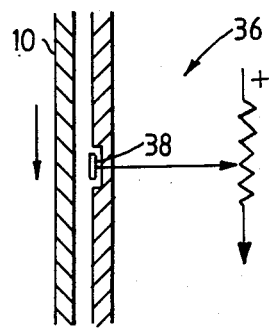
Figure 6:
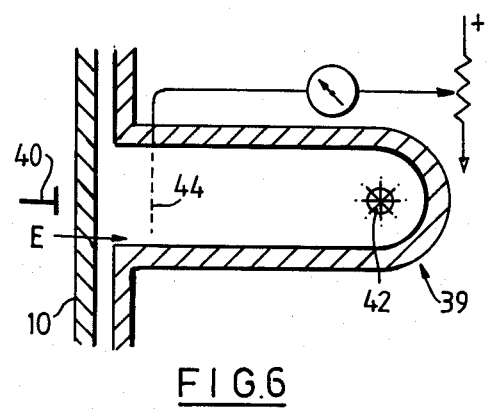

The trap is then rotated through an ionizer 28 as shown in FIG. 4. The ionizer 28 preferably comprises a bank of needle points 30 supplied with a negative ionizing potential of about 3000 volts and, in combination with an earthed electrode 32 on the other side of the disc 10, produces a quiet corona discharge 34. Electrons emitted from the corona discharge will not normally be captured by electrophylic species, such as nitro compounds, when in the gas phase in the environment of the discharge itself. This is because of the high energy of the electrons themselves. There is no mechanism by which the energy can be dissipated during the capture process and in consequence the bond energy is insufficient to bind the electrons. However, this is not the case in the solid surface 11 where the electron energy may be dissipated, thus allowing capture to take place. It is believed that both electrons and negative ions come to rest in the surface of the silica, and since there is supplied a vast excess of electrons as compared with the number of electrophylic molecules in the surface, the probability of capture producing negative ions from nitro compounds can approach unity, i.e. 100% probability of capture.

If the negative ions trapped in the silica surface are to be detected as required, then the considerable excess of electrons held in the silica surface must first be removed. This is accomplished in the electron stripper 36 shown in FIG. 5 which comprises a metal electrode 38 mounted very close to, but not actually in contact with, the rotating silica surface. The potential of this electrode 38 may be varied from zero to a few hundred volts positive. The potential can be increased from zero until all the electrons are removed from the silica surface as they pass underneath the electrode.

Finally, the silica trap 10 is rotated into an ion collector 39 wherein an electric field is provided by means of an electrode 40 on the opposite side of the disc and heating is provided from a high power lamp 42, such as an arc lamp or laser. The surface of the silica glass is heated very rapidly by the arc lamp and the ions are emitted from the hot surface and move under the influence of the electric field to be collected on a collector electrode 44. In some cases, it may be necessary to provide a further positive potential on the collector electrode 44 and for this reason it is preferred for the ion current amplifier (see FIG. 9) of the drift tube detector to be capable of being floated to a positive potential. The current amplifier should preferably be capable of measuring fempto-amp ($10-15_A$) current levels and of giving a direct read-out.

Reference is now directed to FIGS. 7 to 10 for a discussion and description of a preferred form of the ion collector. Preferably, the ion collector is arranged in the form of an ion mobility spectrometer.

Previous designs have used negative ion mobility spectrometers, wherein the negative ions were formed by electron attachment in a plasma produced by a radioactive source. The probability of capture by nitro molecules is extremely high, depending on source strength and residence time in the plasma. However, most of the negative ions which are formed are immediately removed by discharge on the positive ions which are also present in excess. The negative ions which do survive are pulled out of the plasma and await gating into the ion drift tube. The shutter gates are only open for about 3% of the total time and so many more ions are lost to discharge on the walls and through ventilation during the waiting period. Overall, the efficiency of the conversion of nitro molecules into ions collected in the drift tube is less than 0.01%.

Figure 7:
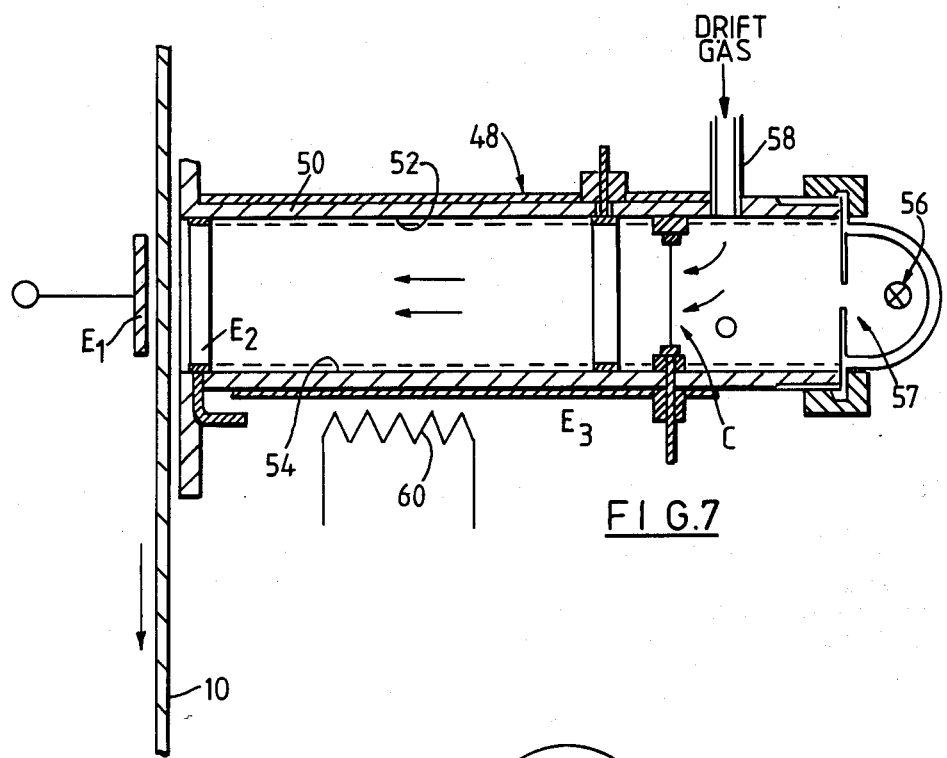
FIG. 7 is a diagrammatic sectional side elevation of a practical embodiment of an ion mobility detector of an apparatus in accordance with the present invention.
Figure 8:
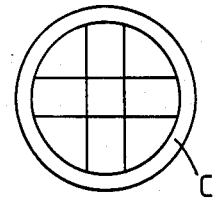
FIG. 8 shows a collector grid forming part of the detector of FIG. 7.

In contrast, in the present apparatus, negative nitro ions are first formed in the surface of the silica trap as described above and excess electrons are removed by the electron stripper whereby only low volatility negative ions remain on the trap when it is rotated in the ion mobility spectrometer. All of the ions in the trap are available for presentation to the drift region and efficiencies approaching 100% are possible, thus increasing detection capability by 10,000 times. A preferred design of ion mobility spectrometer (IMS) is shown in FIG. 7 and includes a drift tube 48 in the form of a ceramic cylinder 50 coated on its inner wall 52 with a very high impedance film 54 which allows an electric field to be maintained down the tube 48 between electrodes $E_2$ and $E_3$. The conductive film is continued beyond electrode $E_3$, thus maintaining a constant potential down the remainder of the tube.

The silica trays 10 forms one end face of the spectrometer and is arranged to be irradiated by short, very intense light beam pulses from a high power flash lamp or laser 56 disposed at the opposite end of the drift tube 48. The light beam is collimated by a collimator 57 so that the beam only strikes the rotating trap and not the walls of the drift tube. The heating effect of the flash, combined with the high initial field produced between the electrode $E_2$ and a further electrode $E_1$ disposed on the other side of the trap 10, causes the nitro ions to be emitted into the drift tube 48 in a very narrow planar pulse or "packet" of ions. The latter pulse, which may be as short as a few micro-seconds, provides extreme resolution capability, being up to 1000 times narrower than the pulses obtained in the existing ion mobility spectrometers. This narrow pulse allows the drift tube to be of smaller size while at the same time yielding a greater resolution.

Figure 9:
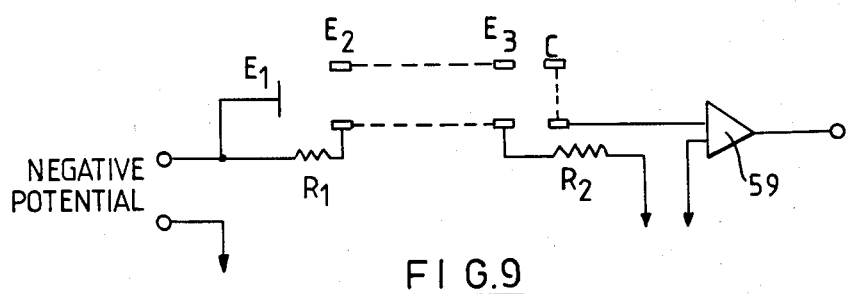
FIG. 9 is a simplified circuit diagram illustrating the energisation of the electrodes in the detector of FIG. 7.

The "packets" of ion periodically liberated by the light pulses are caused to drift down the drift tube under the influence of the electric field provided by the high voltage, connected as shown in FIG. 9 to electrodes $E_1$, $E_2$ and $E_3$.

Ions passing down the tube 48 are collected by an open grid collector C (see also FIG. 8) which is held at earth potential. Electrodes $E_2$ and $E_3$ are ring electrodes and are connected to one another by the above-mentioned very high resistance film or coating 54 on the inner wall of the insulated drift tube, whereby to allow a uniform field to be maintained between the trap and the collector grid C. An electric gradient is maintained between the last ring electrode and the collector electrode C to ensure that substantially all the ions are collected on the collector grid. The collector C is connected to a fast electrometer amplifier 59 which provides an output signal proportional to the ion current collected at the collector.

In operation, a flow of clean, dry drift gas is maintained down the drift tube 48 at all times by way of one or more inlets 58 disposed upstream of the collector grid C and exhausts through narrow gaps between the drift tube and the rotary trap. The drift gaps can be almost any clean dry gas which does not react with the drift ions, but normally is either nitrogen or dry air. Some gas may be directed into the discharge chamber 30 to maintain clean conditions in the latter chamber. The whole drift tube assembly is preferably clad in an earthed jacket to prevent stray fields and pickup and is heatable by a heater 60 to controlled temperatures of up to about 200° C.

The drift tube acts as an ion mobility separator so that when ions are periodically liberated from the flat surface of the trap, they travel down the drift tube under the influence of the drift field and against the flow of drift gas at a velocity which is dependent on the ionic mass. (See E. W. McDaniel and E .A. Mason, THE MOBILITY AND DIFFUSION OF IONS IN GASES, Wiley-Interscience, New York (1973) and H. E. Revercomb and E. A. Mason, THEORY OF PLASMA CHROMATOGRAPHY/GASEOUS ELECTROPHORESIS—Anal.Chem 47, 970-983 (1975)). Ions of differing mobility travel down the tube and separate out and arrive at the collector C, producing an ion current mobility spectrum in which the lighter ions appear first and heavier ions later. In a typical mobility spectrum, all ions are collected within a set period, say 25 ms.

Figure 10:
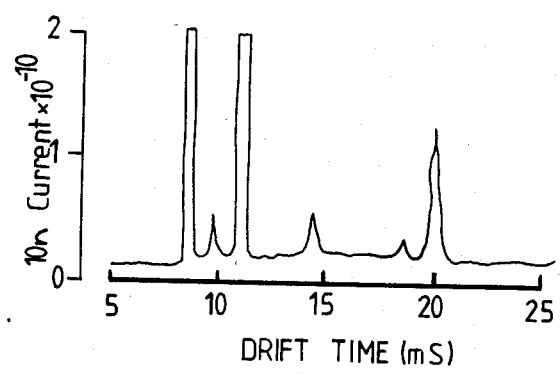
FIG. 10 is a graph illustrating a typical electrical output of the ion mobility detector of FIG. 7.

A typical mobility spectrum is shown in FIG. 10. The mobility spectrum provides a qualitative assessment of the content of the sampled atmosphere. Quantitative measurements of each of the peaks may be made or, alternatively, a drift time window may be monitored to provide an output proportional to the ion current in the window. In this way, a continuous output signal is obtained which is proportional to the amount of certain materials extracted from the airstream by the trap.

The pulse repetition rate of the lamp 56 is set so that the parent ion of specified large nitro ions will be collected between pulses. The speed of rotation of the trap is limited by the pulse repetition rate so that no area of the trap is left unradiated. In some cases, it may be possible to achieve several flashes during the transit through the detector. The potential on electrode $E_1$ is preferably capable of being switched synchronously with the lamp pulses to ensure the adhesion of the nitro molecules between pulses.

One use of the equipment is to study surface contamination of silica substrates in the manufacture of electronic components. In this event the silica under investigation becomes the trap itself.

Inter alia, the apparatus will be useful in the detection of drugs and organo nitro compounds and in connection with plume studies where extreme sensitivity is of paramount importance.

I claim:

1. An apparatus for the detection of airborne, low volatility electrophylic materials, comprising a mobile carrier onto which low volatility electrophylic material to be detected is caused to be deposited, the mobile carrier being arranged to carry said material to a first location where unwanted volatile materials are purged from the mobile carrier and then to a second location where the remaining material is caused to be ionized and then to a third location where the negatively ionized material is caused to be lifted off the mobile carrier into an ion collector.

2. An apparatus according to claim 1, wherein the ionized material on the carrier is lifted off the carrier into an ion collector in the form of an ion drift tube, by means of pulses of electromagnetic radiation from a pulsed arc lamp or laser, so as to produce "packets" of ions which are caused to drift down the drift tube under the influence of an electric field.

3. An apparatus according to claim 1, wherein ionization of the molecules of said material on the carrier is achieved by electron capture and charge transfer from electrons produced in a corona discharge established across a carrier.

4. An apparatus according to claim 1, wherein the mobile carrier is made of an electrical insulating material.

5. An apparatus according to claim 4, wherein said electrical insulating material is selected from the group comprising quartz, P.T.F.E., glass, and a ceramic.

6. An apparatus according to claim 4, wherein said electrical insulating material is silica.

7. An ion mobility spectrometer for use in the detection of airborne, low volatility materials, comprising a solid mobile carrier of an electrically insulating material for trapping in its surface said airborne low volatility materials, a drift tube, a pulsed electromagnetic radiation source disposed adjacent one end of the drift tube and means for displacing said surface of the mobile carrier to a position opposite the other end of the drift tube such that the ions can be released from said surface by the heating effect of electromagnetic radiation pulses from said pulsed electromagnetic radiation source disposed adjacent said one end of the drift tube.

8. An ion mobility spectrometer according to claim 7, wherein at least said surface of said mobile carrier is made of silica.

9. An ion mobility spectrometer according to claim 7, wherein said pulsed electromagnetic radiation source is a pulsed arc lamp.

10. An ion mobility spectrometer according to claim 7, wherein said pulsed electromagnetic radiation source is a pulsed laser.

11. An ion mobility spectrometer for use in the detection of airborne, low volatility materials, comprising a cylindrical drift tube which is made of an electrically insulating material and which is closed at one end and open at the other, a pulsed electromagnetic radiation source and a collector electrode disposed within the drift tube, means for establishing a flow of drift gas through the tube towards the open end, and a solid mobile carrier of an electrically insulating material which is adapted to trap and hold ions of said low volatility materials in its surface, said surface being displaceable to a position adjacent to and facing the open end of the drift tube, and means establishing an electric field within the tube which causes ions released from said surface by the heating effect of pulsed electromagnetic radiation from said radiation source to drift up the tube, against the flow of drift gas, towards said collector electrode.

12. An ion mobility spectrometer according to claim 11, wherein at least said surface of the mobile carrier is made of silica.

13. An ion mobility spectrometer according to claim 11, wherein said means establishing the electric field comprises a first electrode located opposite the open end of the drift tube with the mobile carrier disposed therebetween and second and third electrodes disposed at longitudinally spaced locations within the drift tube.

14. An ion mobility spectrometer according to claim 13, wherein said second and third electrodes are interconnected by way of a very high impedance coating on the inner peripheral wall of the drift tube.

15. An ion mobility spectrometer according to claim 11, including a heater for heating the drift tube to a selected temperature.

16. Apparatus for the detection of airborne, low volatility materials, comprising a mobile carrier surface onto which molecules of a material or materials to be detected are caused to be deposited, means for ionizing said molecules in the carrier surface by causing said surface to be sprayed with electrons from a corona discharge device, means for subsequently stripping excess electrons from the surface, and an ion mobility spectrometer for detecting ions present on said surface.

17. Apparatus according to claim 16, wherein the mobile carrier comprises a flat rotating disc of silica which is cooled by a coolant gas, unwanted contaminants being removed, prior to the ionization step, by means of a heated back-flush of dry gas.

18. Apparatus according to claim 17, wherein the corona discharge is established between a plurality of point electrodes disposed adjacent said surface on one side of the rotating disc and a plate electrode disposed on the other side of said disc.

19. Apparatus according to claim 16, wherein ionized molecules are removed into said ion mobility spectrometer by means of photo desorption and an electric field.

20. An apparatus for the detection of airborne, low volatility electrophylic materials, comprising a mobile carrier onto which low volatility electrophylic material to be detected is caused to be deposited, the mobile carrier being arranged to carry said material to a first location where the material on the carrier is caused to be ionized and then to a second location where the negatively ionized material is caused to be lifted off the carrier into a drift tube detector.

* * * * *